United States Patent
Chevallier et al.

(10) Patent No.: US 7,033,576 B2
(45) Date of Patent: Apr. 25, 2006

(54) USE OF A HIGH STRUCTURE AND DISPERSIBLE PRECIPITATED SILICA AS A THICKENING OR TEXTURING AGENT IN TOOTHPASTE COMPOSITIONS

(75) Inventors: Yvonick Chevallier, Fontaines St-Martin (FR); Adrien Dromard, Lyons (FR); Pierre-Yves Lahary, Lyons (FR); Céline Marcandelli, Paris (FR)

(73) Assignee: Rhodia Chimie, Aubervilliers (FR)

( * ) Notice: Subject to any disclaimer, the term of this patent is extended or adjusted under 35 U.S.C. 154(b) by 617 days.

(21) Appl. No.: 10/296,788

(22) PCT Filed: Jun. 6, 2001

(86) PCT No.: PCT/FR01/01742

§ 371 (c)(1),
(2), (4) Date: Nov. 26, 2002

(87) PCT Pub. No.: WO01/93803

PCT Pub. Date: Dec. 13, 2001

(65) Prior Publication Data

US 2003/0147816 A1    Aug. 7, 2003

(51) Int. Cl.
*A61K 8/00*    (2006.01)
*A61K 8/21*    (2006.01)

(52) U.S. Cl. .......................... 424/49; 424/52

(58) Field of Classification Search .................... None
See application file for complete search history.

(56) References Cited

U.S. PATENT DOCUMENTS

| | | | |
|---|---|---|---|
| 5,419,888 A | 5/1995 | McGill | 423/338 |
| 5,484,581 A | 1/1996 | Esch | 423/335 |
| 5,647,903 A | 7/1997 | McGill | 423/338 |

FOREIGN PATENT DOCUMENTS

| | | |
|---|---|---|
| EP | 0 345 109 | 12/1989 |
| WO | 97/46485 | 12/1997 |
| WO | 99/36360 | 7/1999 |
| WO | 00/64810 | 11/2000 |

OTHER PUBLICATIONS

Patent Abstracts of Japan, vol. 009, No. 108 (C-280), May 11, 1985 & JP 60 001115 A (Central Glass KK), Jan. 07, 1985.
Patent Abstracts of Japan, vol. 011, No. 297 (C-448), Sep. 25, 1987 & JP 62 087507 A (Fuji Debuison Kagaku KK), Apr. 22, 1987.
International Search Report, Apr. 2002.

*Primary Examiner*—Frederick Krass

(57) ABSTRACT

The invention concerns the use, as thickening or texturing agent in toothpaste compositions, of a highly dispersible precipitated silica having a pH of 3.5 to 9, a DOP oil absorption higher than 200 ml/g, a CTAB specific surface area from 70 to 250 m2, a median diameter of at least 20 μm determined by ultrasound-free laser diffraction, a residual anion rate, expressed in sodium sulphate, less than 5 wt. %.

29 Claims, No Drawings

USE OF A HIGH STRUCTURE AND DISPERSIBLE PRECIPITATED SILICA AS A THICKENING OR TEXTURING AGENT IN TOOTHPASTE COMPOSITIONS

This application is an application under 35 U.S.C. Section 371 of International Application No. PCT/FR01/01742 filed on Jun. 6, 2001.

The present invention relates to the use, in toothpaste compositions, of a highly structured, highly dispersible and preferably dense precipitated silica, as a thickener or texturing agent; the invention also relates to a process for thickening toothpaste compositions or for giving toothpaste compositions texture, by incorporating into said compositions a highly structured, highly dispersible and preferably dense precipitated silica, and also to the toothpaste compositions thus obtained.

It is known practice to use silicas, especially highly structured precipitated silicas (DOP oil uptake of at least 200 ml/g), of fine particle size (generally with a median diameter of less than 15 μm) and of low density, as thickeners in toothpaste compositions.

The Applicant has found that highly structured, highly dispersible and preferably dense precipitated silicas with a median diameter of at least 20 μm have entirely noteworthy thickening power in toothpaste compositions.

A first object of the invention consists in using, as a thickener or texturing agent in toothpaste compositions, a precipitated silica having

- a pH from 3.5 to 9, preferably from 4 to 9 and most particularly from 5 to 8
- a DOP oil uptake of greater than 200 ml/g, preferably greater than 230 ml/g and most particularly greater than 250 ml/g
- a CTAB specific surface area from 70 to 250 m$^2$/g and preferably from 100 to 200 m$^2$/g
- a median diameter of at least 20 μm, preferably of at least 25 μm, determined by laser scattering without ultrasound
- a residual anion content, expressed as sodium sulfate, of less than 5% by weight and preferably less than 3% by weight.

The pH of the silica is measured according to ISO standard 787/9 (pH of a suspension containing 5% by weight of silica in deionized water).

The CTAB specific surface area is the outer surface area determined according to NFT standard 45-007 (November 2987).

The silicas according to the invention preferably have a BET specific surface area such that the ratio: BET specific surface area/CTAB specific surface area is from 0.9 to 1.7, preferably from 0.9 to 1.5 and most particularly from 0.9 to 1.4.

The BET specific surface area is determined according to the Brunauer-Emet-Teller method described in "The Journal of the American Chemical Society", Vol. 60, page 309, February 1938 and corresponding to NFT standard 45007 (November 1987).

The DOP oil uptake is determined according to ISO standard 787/5 using dioctyl phthalate.

The silicas according to the invention preferably have a tamped filling density of at least 0.17 g/ml, most preferably of at least 0.18 g/ml and even more particularly of at least 0.19 g/ml, or even of at least 0.20 g/ml; the untamped filling density is preferably at least 0.13 g/ml, most preferably at least 0.15 g/ml and even more particularly at least 0.16 g/ml.

The tamped or untamped filling density is determined according to ISO standard 787/11.

The median diameter is determined by laser scattering according to NF X standard 11-666. The granulometer used may be, for example, of the Sympatec or Malvern type.

Examples of this type of granulometer with the measuring criteria used are given below:

Sympatec Helos Granulometer
  wet dispersion: Sucell

Measurement Criteria
  optical concentration: 20%
  measurement liquid: degassed demineralized water
  absence of ultrasound
  absence of dispersant
  focal length: 100 mm
  measuring time: 20 seconds Malvern Mastersizer Microplus Granulometer Measurement Criteria
  optical concentration: 12±2%
  measurement liquid: degassed demineralized water
  absence of ultrasound
  absence of dispersant
  measuring time: 10 seconds For good implementation of the invention, said silica has an ultrasound-mediated disintegration factor $F_D$ of at least 8 and preferably of at least 9.5, with particle size measurement by laser scattering using a Sympatec granulometer.

The disintegration factor $F_D$ is determined according to the following protocol: the disintegratability or the dispersibility of the silica particles is assessed by means of a particle size measurement (by laser scattering), carried out on a suspension of silica disintegrated beforehand by ultrasonication; the disintegratability of the silica (rupture of objects from 0.1 to a few tens of microns in size) is thus measured. The ultrasound-mediated disintegration is performed using a Vibracell Bioblock sonicator (600 W) equipped with a probe 19 mm in diameter. The particle size measurement is performed by laser scattering on a Sympatec granulometer.

Two grams of silica are weighed out in a pill bottle (height: 6 cm and diameter: 4 cm) and the weight is made up to 50 grams by adding deionized water: an aqueous 4% silica suspension is thus prepared, and is homogenized for 2 minutes by magnetic stirring. The ultrasound-mediated disintegration is then performed as follows: with the probe immerged to a depth of 4 cm, the output power is adjusted so as to obtain a deflection of the power dial needle indicating 20%. The disintegration is performed for 420 seconds. The particle size measurement is then performed by introducing a volume V (expressed in ml) of the homogenized suspension required to obtain an optical concentration of 20% into the granulometer cuvette.

The disintegration factor $F_D$ is then given by the equation:

$$F_D = 10 \times V/\text{optical concentration of the suspension measured by the granulometer (this optical concentration is about 20\%).}$$

This disintegration factor $F_D$ is indicative of the content of particles less than 0.1 μm in size that are not detected by the granulometer. This factor is proportionately higher the higher the disintegratability of the silica.

The median diameter $\varnothing_{50}$ obtained according to this test is proportionately smaller the greater the disintegratability of the silica.

The dispersibility of the silica according to the invention in a toothpaste formulation may also be determined by measuring the median diameter d50 of the silica on the Malvern Mastersizer granulometer after ultrasound-mediated disintegration according to the following dispersion test:

With the ultrasound power in the Malvern Mastersizer granulometer set to the maximum setting of 20, an amount of silica is introduced so as to obtain an optical concentration of 12±2%.

The median diameter d50 and the percentage of silica particles with a diameter of greater than 51 μm are measured after having maintained the ultrasound in the cuvette for 60 seconds, the cuvette being homogenized by circulating the suspension using a centrifugal pump. The measurement is recorded 10 seconds after switching off the ultrasound.

For a good implementation of the invention, the median diameter is favorably not more than 40 μm and preferably not more than 35 μm. The weight percentage of silica particles greater than 51 μm in diameter is favorably not more than 30 and preferably not more than 25.

Said highly structured, highly dispersible and preferably dense silica may be obtained by reacting an aqueous solution of an alkali metal silicate with an acidifying agent to form a silica slurry, followed by separation, optional acidification and drying of the silica cake, said slurry being formed at a temperature from 60 to 98° C., by reacting an aqueous solution of an alkali metal silicate with an acidifying agent according to the following steps (slurry-forming operation):

(a) a first step, consisting in using an initial stock solution comprising water and all or some of the alkali metal silicate, in a concentration, expressed as silica, of less than or equal to 100 g/l and preferably less than or equal to 80 g/l;

(b) a second step consisting in introducing, in a continuous or batchwise manner, an acidifying agent until the pH obtained in the medium is at least 7 and preferably from 7 to 9.2;

(c) where appropriate, a third step, consisting in simultaneously introducing the remaining amount of silicate and an acidifying agent, while keeping the temperature of the reaction medium constant and maintaining a pH of at least 7 and preferably from 7 to 9.2;

(d) and a final step of acidifying the reaction medium by adding an acidifying agent until the pH obtained in the slurry is from 3 to 6 and preferably from 4 to 6;

and then being separated by filtration/washing and fluidized until a silica cake with a loss on ignition of greater than 80% and preferably of at least 82%, and a residual anion content, expressed as sodium sulfate, of less than 5% by weight and preferably less than 3% by weight, relative to the weight of final product, are obtained.

The choice of the acidifying agent and of the silicate for performing the slurry-forming operation is made in a manner that is known per se.

It may be recalled that a strong mineral acid such as sulfuric acid, nitric acid or hydrochloric acid, or an organic acid such as acetic acid, formic acid or carbonic acid, is generally used as acidifying agent.

The acidifying agent may be used in dilute or concentrated form.

In particular, when it is sulfuric acid, it may be used in the form of an aqueous solution containing from 40 to 400 g/l and preferably from 60 to 150 g/l of acid.

Any common form of silicate in aqueous solution may be used as silicate, such as metasilicates, disilicates and advantageously an alkali metal silicate, especially a sodium or potassium silicate.

The silicate solution may have a concentration, expressed as silica, of between 20 and 350 g/l, for example between 60 and 300 g/l and in particular between 100 and 260 g/l.

In the case where sodium silicate is used, it generally has an $SiO_2/Na_2O$ weight ratio of between 2 and 4, for example between 3.0 and 3.7.

More particularly, sulfuric acid is used as acidifying agent and a sodium silicate is used as silicate.

The first step of the slurry-forming operation (step (a)) consists in using a stock solution comprising water and silicate.

Preferably, the amount of silicate (expressed as $SiO_2$) present in the initial stock solution represents only a part of the total amount of silicate (expressed as $SiO_2$) used in the reaction.

This partial amount of silicate (expressed as $SiO_2$) can represent, for example, up to 95% of the total amount of silicate; this amount is preferably at least 5% of the total amount of silicate (expressed as $SiO_2$).

The silicate concentration in the initial stock solution is less than or equal to 100 g of $SiO_2$ per liter. Preferably, this concentration is less than or equal to 80 g/l. It is preferably at least 5 g/l.

The second step (step (b)) consists in adding the acidifying agent to the stock solution.

This addition, which results in a correlated reduction in the pH of the reaction medium, is performed until the pH value achieved is preferably from 7 to 9.2.

The third step (step (c)) is performed if the starting stock solution comprises only a portion of the total amount of silicate used in the reaction.

The simultaneous addition of acidifying agent and of the remaining amount of silicate is preferably performed such that the pH value is constantly equal (to within ±0.2 pH units) of that achieved after step (b).

This step is performed at a constant temperature preferably corresponding to that at the end of step (b).

In the final acidification step (d), an additional amount of acidifying agent is added to the reaction medium obtained from step (c) if only a portion of the total amount of silica was used in the stock solution, or from step (b) if the total amount of silica was used in the stock solution, until the pH value obtained in the reaction medium is between 3 and 6 and preferably between 4 and 6.

It may be advantageous to perform one or more intermediate maturation steps during the slurry-forming operation.

Thus, steps (b) and/or (c) and/or (d) may be followed by a maturation step.

It is especially advantageous to perform a maturation of the reaction medium after the final acidification step (d), this maturation possibly lasting, for example, from 1 to 30 minutes and especially from 2 to 15 minutes.

It may also be beneficial to perform a maturation of the reaction medium after step (b) of first addition of acid.

The temperature of the reaction medium during the slurry-forming operation is generally between 60 and 98° C. The same temperature may be maintained throughout the reaction or a nonuniform temperature profile may be adopted.

According to a first embodiment, the slurry-forming operation is performed at a constant temperature, preferably of between 75 and 98° C.

According to a second (preferred) embodiment, the reaction end temperature is higher than the reaction start temperature; thus, the temperature at the start of the operation is preferably maintained between 60 and 80° C., and the temperature is then increased, preferably to reach a value of between 75 and 98° C., especially at the end of step (b) of first addition of acid, at which value the temperature is maintained until the end of the reaction.

One embodiment variant of the slurry-forming operation consists in performing at least one of the steps (a) to (c) above in the presence of an electrolyte.

The term "electrolyte" is understood here in its normal accepted meaning, i.e. it means any ionic or molecular substance which, when dissolved in water, decomposes or dissociates to form charged particles or ions.

Among the electrolytes that may especially be mentioned are alkali metal or alkaline-earth metal salts, especially the metal salt of the starting silicate and of the acidifying agent, i.e. preferably sodium sulfate; sodium chloride, sodium nitrate and sodium hydrogen carbonate are also advantageous.

Said electrolyte is used in at least one of the steps (a) to (c) in an amount that may be from about 0.05 to 0.3 mol/liter when it is an electrolytic salt of an alkali metal, or from about 0.005 to 0.05 mol/liter when it is an electrolytic salt of an alkaline-earth metal.

The electrolyte is preferably used in the stock solution (step (a)).

According to this embodiment variant (use of an electrolyte in at least one of the steps (a) to (c)), the concentration of alkali metal silicate, expressed as silica, in said stock solution in step (a) is preferably greater than or equal to 40 g/l; the pH of the reaction medium in steps (b) and (c) is preferably from about 7 to 8.5 and most particularly from 7 to 8.

Various embodiments of the slurry-forming operation according to the invention are described in EP-A-520 862, FR-A-2 710 629, EP-A-670 813, EP-A-670 814 and WO 98/5409.

The silica slurry thus formed is then separated by filtration/washing.

This step may be performed according to any suitable method, for example using a filter press, a band filter, a rotary filter under vacuum, etc. Said filtration/washing operation is preferably performed using a rotary filter under vacuum.

The washing is performed until the residual anion content, expressed as sodium sulfate, present in the filter cake obtained is less than 5% by weight and preferably less than 3% by weight, expressed relative to the final product.

The filter cake is then fluidized.

The fluidization step may be performed by mechanical action by treating the cake in a mill, for example of colloidal or ball type, or by mechanical action in a crumbling machine equipped with scraping systems, doctor blades, etc.

This operation may also be performed by adding water or an aqueous solution of an acid, especially sulfuric acid, in order to obtain a silica cake with a loss on ignition of greater than 80% and preferably of at least 82%.

If necessary, the pH of the cake may be reduced to 3 by adding acid in this step. It will be necessary in this step (and also in the filtration/washing step) to take account of the limit content of residual anion not to be exceeded. This fluidization step must be performed in the absence of aluminum salts.

The silica cake is then dried by a rapid drying means, most particularly by spraying.

The spray-drying of the silica may be performed in a known manner using various types of sprayer. A person skilled in the art knows how to adapt the type of sprayer depending on the type of objects desired (powders or beads).

With turbomixer sprayers or nozzle sprayers, powders with a median diameter of greater than 20 µm and preferably greater than 25 µm, which may be up to 250 µm, or beads with a median diameter that may be up to 600 µm, may be obtained.

The powders or beads obtained are not ground.

The silica according to the invention, whether in the form of powder or beads (preferably in the form of powder), has the property of disintegrating and/or dispersing into elements of smaller size (than the starting size), within the toothpaste compositions, during the preparation of said compositions, and thus makes it possible to thicken said compositions or to give them texture.

Said silica may be readily disintegrated and dispersed into elements with a median diameter of less than 50 µm, generally less than 20 µm and most particularly less than 15 µm, by suitable shear in the toothpaste during preparation.

Preferably, said silica in disintegrated and dispersed form in a toothpaste formulation (gel or opaque) does not have more,than 20%, preferably not more than 15% and most particularly not more than 6% by weight, of elements greater than 51 µm in diameter.

The measurement of the particle size of the silica in disintegrated and dispersed form in the toothpaste composition is determined by laser scattering according to NF X standard 11-666 using a laser granulometer without ultrasound (as already described above). This measurement is performed on an aqueous dispersion containing 10% by weight of the toothpaste formulation; before the measurement, this dispersion, placed in flasks, was agitated beforehand for 15 minutes by placing said flasks in a vibrating agitator.

The toothpastes obtained have a smooth appearance and do not have a granular mouthfeel.

According to the invention, said silica may be used as a thickener or texturing agent in a proportion of from 0.1% to 20%, preferably from 0.5% to 15% and most particularly from 1% to 10%, relative to the weight of the toothpaste composition.

Said toothpaste composition may also comprise other usual ingredients, in particular water-insoluble mineral abrasive agents, optionally other thickeners, wetting agents, etc.

Abrasive agents that may be mentioned in particular include abrasive silicas, calcium carbonate, hydrated alumina, bentonite, aluminum silicate, zirconium silicate, and sodium, potassium, calcium or magnesium metaphosphate or phosphate. The total amount of abrasive powder(s) may be from about 5% to 50% relative to the weight of the dental composition.

Among the other thickeners that may be mentioned are xanthan gum, guar gum, carrageenans, cellulose derivatives and alginates, in an amount that may be up to 5% relative to the weight of said composition.

Among the wetting agents that may be mentioned, for example, are glycerol, sorbitol, polyethylene glycols, polypropylene glycols and xylitol, in an amount from about 2% to 85% and preferably from about 3% to 55%, relative to the weight of the toothpaste composition expressed as dry matter.

These compositions may also comprise surfactants, detergents, colorants, antibacterial agents, fluorinated derivatives, opacifiers, flavorings, sweeteners, antitartar agents, anti plaque agents, bleaching agents, sodium bicarbonate, antiseptics, enzymes, natural extracts (camomile, thyme, etc.), etc.

A second subject of the invention consists of a process for thickening toothpaste compositions or for giving toothpaste compositions texture, by incorporating into said compositions highly structured, dense and highly disintegratable and/or dispersible thickening silica, the characteristics of which were explored above.

A final subject of the invention consists of toothpaste compositions comprising highly structured, highly disintegratable and/or dispersible and preferably dense thickening silica, the characteristics of which were explored above, in disintegrated and/or dispersed form in the form of elements with a median diameter of less than 50 μm, generally less than 20 μm and most particularly less than 15 μm. Preferably, the amount of elements with a diameter of greater than 51 μm does not exceed 20%, preferably 15% and most. particularly 6% by weight.

Said compositions may comprise from 0.1% to 20%, preferably from 0.5% to 15% and most particularly from 1% to 10% of said highly structured, highly dispersible and preferably dense silica.

The examples that follow are given for illustrative purposes.

|  | parts by weight |
|---|---|
| Model toothpaste formulation (gel) | |
| CMC (Blanose 12M31P sold by Hercules) | 0.8 |
| Sorbitol (Neosorb 70/70 sold by Roquette Frères) | 65.5 |
| Sodium saccharinate | 0.2 |
| Sodium benzoate | 0.1 |
| Sodium monofluorophosphate (MFP) | 0.76 |
| $H_2O$ | 7.98 |
| Abrasive silica (Tixosil 63 sold by Rhodia) | 10 |
| Silica of the invention | 9 |
| Colorant FDC blue dye No. 1 (0.12% in $H_2O$) | 0.8 |
| Flavoring: spearmint (sold by Mane) | 0.7 |
| Foaming agent: Sipon LCS 98 * (30% in water) from Sidobre-Sinnova | 4.16 |
| Model toothpaste formulation (paste) | |
| Sorbitol (Neosorb 70/70 sold by Roquette Frères) | 45 |
| Polyethylene glycol PEG 1500 | 5 |
| Sodium saccharinate | 0.2 |
| Sodium fluoride | 0.08 |
| Sodium monofluorophosphate | 0.72 |
| Water | 24.2 |
| Abrasive silica (Tixosil 63 sold by Rhodia) | 10 |
| Silica of the invention | 7 |
| Titanium dioxide | 1 |
| Spearmint flavoring | 1 |
| Foaming agent (30% in water): Texapon Z 95 P from Cognis | 5 |

Measurement of the Viscosity of a Toothpaste Formulation

The viscosity is determined on a tube of paste 25 mm in diameter, at given periods at 37° C. after preparation of the paste or the gel.

The measuring equipment used is a Brookfield RVT viscometer equipped with a helipath device. The T-E rotor is used at 5 rpm. The measurement is performed by descent after 90 seconds.

EXAMPLE 1

The following are introduced into a stainless-steel reactor fitted with an impeller stirring system and a jacket heating system:

660 liters of water 11.8 kg of $Na_2SO_4$ (electrolyte)

323 liters of aqueous sodium silicate, with an $SiO_2/Na_2O$ weight ratio equal to 3.45 and a density at 20° C. equal to 1.230.

The $SiO_2$ concentration in the stock solution is thus 77 g/l. The mixture is then brought to a temperature of 82° C. with continued stirring. 395 liters of dilute sulfuric acid with a density at 20° C. equal to 1.050 are then added thereto until the pH value obtained in the reaction medium (measured at its temperature) is equal to 7.5.

77 liters of aqueous sodium silicate of the type described above and 106 liters of sulfuric acid, also of the type described above, are then introduced together into the reaction medium, this simultaneous introduction of acid and silicate being performed such that the pH of the reaction medium, during the introduction period, is constantly equal to 7.5±0.1. After introducing all of the silicate, the introduction of the dilute acid is continued at a rate of 310 l/h, for 5 minutes.

This additional introduction of acid then brings the pH of the medium to a value equal to 5.0.

The total reaction time is set at 85 minutes.

A reaction slurry is obtained, which is filtered and washed using a rotary filter under vacuum.

The filter cake is then fluidized by mechanical action. A pumpable silica cake with a loss on ignition of 86% is obtained, and this cake is then dried using a nozzle sprayer.

The silica obtained has the following characteristics:

BET specific surface area=159 $m^2/g$

CTAB specific surface area=156 $m^2/g$

DOP oil uptake=320 ml/100 g, pH=7.0

$Na_2SO_4$=2.8% by weight

D50 (μm)=123 μm (measured using the Sympatec Helos machine)

Malvern particle size with ultrasound:

.d50=33 μm

.% of particles >51 μm=22 untamped density=0.19 tamped density=0.21 disintegration factor $F_D$=13.3 (measured using the Sympatec Helos machine).

The thickening power provided by adding 9 parts by weight of thickening silica to the model toothpaste gel formulation given above and evaluated by measuring the viscosity of the toothpaste formulation as mentioned above after 3 weeks at 37° C., is given in the table below and compared with the viscosity provided under the same conditions by a commercial thickening silica, the silica Tixosil 43 sold by Rhodia and having the following characteristics:

BET specific surface area=276 $m^2/g$,

CTAB specific surface area=198 $m^2/g$,

DOP oil uptake=348 ml/100 g, pH=7.0

$Na_2SO_4$=2.8% by weight.

This commercial silica was obtained by using the total amount of silicate in the stock solution, said stock solution containing more than 100 g/l of silicate (expressed as silica), and grinding.

| Thickening silica | Example 1 | Tixosil 43 |
|---|---|---|
| D50 (μm) Sympatec Helos | 123 μm | 10 μm |
| Untamped density | 0.19 | 0.10 |
| Tamped density | 0.21 | 0.12 |
| $F_D$ | 13.3 | 3 |
| Median diameter in the toothpaste gel formulation (μm) (Sympatec Helos) | 9.8 | 9.4 |
| % of elements with a diameter >51 μm in the toothpaste gel formulation (Sympatec Helos) | 1 | 1.2 |
| Brookfield viscosity (mPa · s) of the toothpaste gel formulation | 1 100 000 | 500 000 |

It is thus found that, for similar DOP oil uptakes, the nonground, dense and highly dispersible silicas according to the invention have a thickening power that is very markedly superior to a commercial ground thickening silica.

In both cases, the toothpaste (gel) obtained has a smooth appearance; no granular mouthfeel is noted.

Having available a highly thickening dense silica represents a particularly important economic advantage: in particular, less powdering, savings in transportation expenses (reduced volume) and smaller amounts of silica to be used to achieve the same level of viscosity of the toothpaste composition.

EXAMPLE 2

The following are introduced into a stainless-steel reactor fitted with an impeller stirring system and a jacket heating system:
15 liters of silicate with a density at 20° C. equal to 1 230 kg/m³ and with an $SiO_2/Na_2O$ weight ratio equal to 3.5, 529 liters of water.

The $SiO_2$ concentration in the stock solution is 6.4 g/l.

The mixture obtained, which is kept stirring, is brought to 75° C. by heating via the jacket. When this temperature is reached, the precipitation reaction is performed. Dilute sulfuric acid with a density at 20° C. equal to 1 050 kg/m³ is introduced at a flow rate of 142 l/h until the pH value obtained in the reaction medium is equal to 8.7.

Aqueous sodium silicate of the type described above is then introduced into the reaction medium at a flow rate of 388 l/h, together with sulfuric acid, also of the type described above, at a flow rate adjusted so as to keep the pH value of the reaction medium equal to 8.7. After simultaneous addition for 55 minutes, the introduction of the silicate is stopped.

The introduction of the dilute sulfuric acid with a density at 20° C. equal to 1.05 is then maintained so as to bring the pH value to 4.3. The reaction slurry is then maintained at this pH for 5 minutes.

A reaction slurry is thus obtained, which is filtered and washed using a rotary filter under vacuum such that a silica cake whose loss on ignition is 85.4% is finally recovered.

This cake is then fluidized by mechanical action. During this crumbling operation, sulfuric acid is introduced so that the pH obtained for the crumbled cake is 3.1. The fluidized and acidified cake is then dried using a nozzle sprayer 1.3 mm in diameter.

The characteristics of the silica obtained are as follows:
BET specific surface area=205 m²/g
CTAB specific surface area=165 m²/g
DOP oil uptake=311 ml/100 g
pH=4.0
$Na_2SO_4$=0.9%
untamped density=0.19
tamped density=0.21
Malvern particle size without ultrasound d50=180 μm
Malvern particle size with ultrasound d50=27 μm %>51 μm=12
disintegration factor $F_D$=16.8 (Sympatec).

The Brookfield viscosities obtained on the opaque paste and gel formulations described above are given in the following table:

| | Example 2 | Tixosil 43 |
|---|---|---|
| 1. Gel formulation | | |
| Brookfield viscosity (mPa · s) after 1 week at 37° C. | 780 000 | 420 000 |
| Sympatec particle size | | |
| d50 (μm) | 8.3 | 8.4 |
| Appearance of the gel | Smooth | Smooth |
| Mouthfeel | Nongranular | Nongranular |
| 2. Opaque paste formulation | | |
| Brookfield viscosity (mPa · s) after 4 weeks at 37° C. | 500 000 | 310 000 |
| Malvern particle size | | |
| d50 (μm) | 8.9 | 7.8 |
| % of particles >51 μm | 3.9 | 0.4 |
| Appearance of the paste | Smooth | Smooth |
| Mouthfeel | Nongranular | Nongranular |

EXAMPLE 3

The following are introduced into a stainless-steel reactor fitted with an impeller stirring system and a jacket heating system:
15 liters of silicate with a density at 20° C. equal to 1 230 kg/m³ and with an $SiO_2/Na_2O$ weight ratio equal to 3.5, 529 liters of water.

The $SiO_2$ concentration in the stock solution is 6.4 g/l.

The mixture obtained, which is kept stirring, is brought to 75° C. by heating via the jacket. When this temperature is reached, the precipitation reaction is performed. Dilute sulfuric acid with a density at 20° C. equal to 1 050 kg/m³ is introduced at a flow rate of 142 l/h until the pH value obtained in the reaction medium is equal to 8.7.

Aqueous sodium silicate of the type described above is then introduced into the reaction medium at a flow rate of 388 l/h, together with sulfuric acid, also of the type described above, at a flow rate adjusted so as to keep the pH value of the reaction medium equal to 8.7. After simultaneous addition for 55 minutes, the introduction of the silicate is stopped.

The introduction of the dilute sulfuric acid with a density at 20° C. equal to 1.05 is then maintained so as to bring the pH value to 3.9. The reaction slurry is then maintained at this pH for 5 minutes.

A reaction slurry is thus obtained, which is filtered and washed using a rotary filter under vacuum such that a silica cake whose loss on ignition is 85.4% is finally recovered.

This cake is then fluidized by mechanical action. During this crumbling operation, sulfuric acid is introduced so that the pH obtained for the crumbled cake is 3.8. The fluidized and acidified cake is then dried using a turbomixer sprayer rotating at 9 000 rpm.

The characteristics of the silica obtained are as follows:
BET specific surface area=205 m$^2$/g
CTAB specific surface area=164 m$^2$/g
DOP oil uptake=316 ml/100 g
pH=6.0
Na$_2$SO$_4$=1.4%
untamped density=0.16
tamped density=0.23
Malvern particle size without ultrasound d50=34.4 μm
Malvern particle size with ultrasound .d50=23.8 μm .%>51 μm=5
disintegration factor F$_D$=14.5 (Sympatec).

The Brookfield viscosities obtained on the opaque paste and gel formulations described above are given in the following table:

|  | Example 3 | Tixosil 43 |
|---|---|---|
| 1. Gel formulation |  |  |
| Brookfield viscosity (mPa · s) after 1 week at 37° C. | 760 000 | 420 000 |
| Sympatec particle size |  |  |
| d50 (μm) | 6.9 | 8.4 |
| % >51 μm | 0 | 0 |
| Appearance of the gel | Smooth | Smooth |
| Mouthfeel | Nongranular | Nongranular |
| 2. Opaque paste formulation |  |  |
| Brookfield viscosity (mPa · s) after 4 weeks at 37° C. | 500 000 | 310 000 |
| Malvern particle size |  |  |
| d50 (μm) | 8.3 | 7.8 |
| % of particles > 51 μm | 3.3 | 0.4 |
| Appearance of the paste | Smooth | Smooth |
| Mouthfeel | Nongranular | Nongranular |

The invention claimed is:

1. A toothpaste composition, comprising, as a thickener or texturing agent,
   a precipitated silica having
   a pH from 3.5 to 9,
   a DOP oil uptake of greater than 200 ml/g,
   a CTAB specific surface area from 70 to 250 m$^2$/g,
   a median diameter of at least 20 μm, and
   a residual anion content, expressed as sodium sulfate, of less than 5% by weight.

2. The composition as claimed in claim 1, wherein said silica has a tamped filling density of at least 0.17 g/ml.

3. The composition as claimed in claim 2, wherein said silica has a tamped filling density of at least 0.20 g/ml.

4. The composition as claimed in claim 1, wherein said silica has an ultrasound-mediated disintegration factor F$_D$ of at least 8.

5. The composition as claimed in claim 1, wherein said silica has a median diameter after ultrasound-mediated disintegration of not more than 40 μm.

6. The composition as claimed in claim 5, wherein said silica has, after ultrasound-mediated disintegration, a weight percentage of particles greater than 51 μm in diameter of not more than 30%.

7. The toothpaste composition according to claim 1, wherein the precipitated silica has:
   a pH from 5 to 8,
   a DOP oil uptake of greater than 250 ml/g,
   a CTAB specific surface area from 100 to 200 m$^2$/g,
   a median diameter of at least 25 μm,
   a residual anion content, expressed as sodium sulfate, of less than 3% by weight,
   a tamped filling density of at least 0.19 g/ml,
   an ultrasound-mediated disintegration factor F$_D$ of at least 9.5, and
   a median diameter after ultrasound-mediated disintegration of not more than 35 μm.

8. The composition as claimed in claim 1, wherein said silica is obtained by reacting an aqueous solution of an alkali metal silicate with an acidifying agent to form a silica slurry, followed by separation, optional acidification and drying of the silica cake, said slurry being formed at a temperature from 60 to 98° C., by reacting an aqueous solution of an alkali metal silicate with an acidifying agent according to the following steps:
   (a) starting with an initial stock solution comprising water and all or some of the alkali metal silicate, in a concentration, expressed as silica, of less than or equal to 100 g/l;
   (b) adding, in a continuous or batchwise manner, an acidifying agent until a pH of at least 7 is obtained;
   (c) simultaneously adding the remaining amount of silicate and an acidifying agent, while keeping the temperature of the reaction medium constant and maintaining a pH of at least 7;
   (d) acidifying the reaction medium by adding an acidifying agent until the pH obtained in the slurry is from 3 to 6; and, then
   (e) separating by filtration/washing a silica cake with a loss on ignition of greater than 80% and a residual anion content, expressed as sodium sulfate, of less than 5% by weight, relative to the weight of final product.

9. The composition as claimed in claim 8, wherein the silicate is a sodium silicate with a SiO$_2$/Na$_2$O weight ratio of between 2 and 4.

10. The composition as claimed in claim 8, wherein the acidifying agent is sulfuric acid.

11. The composition as claimed in claim 8, wherein the amount of silicate present in the stock solution represents from 5% to 95% of the total amount of silicate used.

12. The composition as claimed in claim 8, wherein the concentration of alkali metal silicate in the stock solution in step (a) is at least 5 g of SiO$_2$ per liter.

13. The composition as claimed in claim 8, wherein at least one of the steps (a) to (c) is performed in the presence of an electrolyte.

14. The composition as claimed in claim 13, wherein the concentration of alkali metal silicate in the stock solution in step (a) is greater than or equal to 40 g of SiO$_2$ per liter.

15. The composition as claimed in claim 13, wherein the electrolyte is present in the stock solution in step (a).

16. The composition as claimed in claim 13, wherein the electrolyte present in the medium in at least one of steps (a) to (c) in an amount of from about 0.05 to 0.3 mol/liter when it is an electrolytic salt of an alkali metal, or from about 0.005 to 0.05 mol/liter when it is an electrolytic salt of an alkaline-earth metal.

17. The composition as claimed in claim 13, wherein the pH of the reaction medium in steps (b) and (c) is from about 7 to 8.5.

18. The composition as claimed in claim 8, wherein steps (b), (c) or (d) are followed by a maturation step.

19. The composition as claimed in claim 8, wherein the slurry-forming operation is performed at a constant temperature of between 75 and 98° C.

20. The composition as claimed in claim 8, wherein the temperature at the start of the slurry-forming operation is between 60 and 80° C., and then increases to reach a value of between 75 and 98° C. at the end of step (b) of first addition of acid, at which value the temperature is maintained until the end of the reaction.

21. The composition as claimed in claim 8, wherein, after filtration/washing and fluidization, the silica is spray-dried.

22. The composition as claimed in claim 1, wherein said silica is in the form of a powder with a diameter ranging up to 250 μm or of beads with a diameter ranging up to 600 μm.

23. The composition as claimed in claim 1, wherein said silica is present in a proportion of from 0.1% to 20%, by weight in said toothpaste compositions.

24. The composition as claimed in claim 1, wherein said silica is in disintegrated or dispersed form in said toothpaste compositions, in the form of elements with a median diameter of less than 50 μm.

25. The composition as claimed in claim 24, wherein said silica in disintegrated or dispersed form does not contain more than 20% by weight, of elements greater than 51 μm in diameter.

26. A process for thickening toothpaste compositions or for giving toothpaste compositions texture, comprising the step of incorporating into said compositions an efficient thickening amount of a precipitated silica having:

a pH from 3.5 to 9, a DOP oil uptake of greater than 200 ml/g, a CTAB specific surface area from 70 to 250 $m^2/g$, a median diameter of at least 20 μm, and a residual anion content, expressed as sodium sulfate, of less than 5% by weight.

27. The process according to claim 26, wherein the thickening silica is in a disintegrated or dispersed form and in the form of elements with a median diameter of less than 50 μm.

28. The process as claimed in claim 27, wherein said silica does not contain more than 20% by weight of elements greater than 51 μm in diameter.

29. The process as claimed in claim 28, comprising incorporating from 1% to 10% by weight, of said silica into said toothpaste composition.

* * * * *